United States Patent [19]
Simonson et al.

[11] 4,138,476
[45] Feb. 6, 1979

[54] PLAQUE DISPERSING ENZYMES AS ORAL THERAPEUTIC AGENTS BY MOLECULAR ALTERATION

[75] Inventors: Lloyd G. Simonson, Waukegan; Burton L. Lamberts, Libertyville, both of Ill.

[73] Assignee: The United States of America as represented by the Secretary of the Navy, Washington, D.C.

[21] Appl. No.: 821,275

[22] Filed: Aug. 3, 1977

[51] Int. Cl.$^2$ ................................................ A61K 7/28
[52] U.S. Cl. ........................................ 424/50; 424/94
[58] Field of Search .................................... 424/50, 94

[56] References Cited

U.S. PATENT DOCUMENTS 3,751,561  8/1973  Wildi et al. ............................ 424/48
4,004,979  1/1977  Avrameas et al. ...................... 424/94

FOREIGN PATENT DOCUMENTS 5151512  5/1976  Japan ........................................ 424/94

OTHER PUBLICATIONS

J. Termine et al., Chemical Abstracts 73: 126985a (1970); Calcium phosphate formation in vitro.
R. Peckauskas et al., Chemical Abstracts 84: 117398m (1976); ESR Investigation of the Binding of Acidic Biopolymers to Synthetic Apatite.
C. Nawrot et al., Chemical Abstracts 85: 107042x; Dental Phophoprotein–induced Formation of Hydroxylapatite During in Vitro Synthesis of Amorphous Calcium Phosphate.
J. Glaimcher et al., Chemical Abstracts 77: 57958n (1972); Role of the Organic Matrices in Mineralization.
K. Grizzuti et al., Chemical Abstracts 80: 3790 (1974); Binding of Calcium and Magnesium Ions to the Phosphoglycoprotein Phosvitin.
L. Wiggins, Chemical Abstracts 75: 101285a (1971); Compositions for use on Teeth to Prevent Caries.

Primary Examiner—Elbert L. Roberts
Assistant Examiner—Molly C. Eakin
Attorney, Agent, or Firm—Richard S. Sciascia; George A. Montanye

[57] ABSTRACT

An oral therapeutic substance is formed by modifying a plaque-dispersing enzyme to control and reduce the occurrence of dental caries and periodontal diseases. In one embodiment, the modification is performed by introducing a suitable complexing reagent in combination with carrier and plaque-dispersing glucanohydrolase molecules to molecularly alter the glucanohydrolase. The modification, while having insignificant effects on the catalytic activity of the enzyme, will increase the binding capability of the enzyme to substances of which the tooth surface is formed. The activity of the enzyme on the tooth surface will therefore be maintained for longer periods of time to combat plaque build-up.

23 Claims, No Drawings

PLAQUE DISPERSING ENZYMES AS ORAL THERAPEUTIC AGENTS BY MOLECULAR ALTERATION

BACKGROUND OF THE INVENTION

The present invention relates to an oral dental preparation for the prevention of dental caries and periodontal diseases and, more particularly, to modified plaque-dispersing enzymes having lengthened activity in oral environments.

During recent years, it has been found that the organisms often associated with the formation of dental caries are certain streptococci belonging to the *Streptococcus mutans* group which contribute to the build-up of plaque and have been implicated in the development of dental caries and periodontal diseases. Specific strains of *Streptococcus mutans* can synthesize adhesive glucans which facilitate adherence of the organisms to tooth surfaces and contribute to the build-up of plaque. The significance of such glucans in relation to dental disease has been demonstrated through various investigations with "glucan synthesis-defective" mutants which have exhibited only low levels of virulence in animal experiments. Other streptococcal strains are additionally thought to synthesize fructan (levan) polysaccharides. Still other Actinomyces strains are major constituents of dental plaque and can be related to both root surface caries and periodontal disease. Such organisms also contribute to the formation of plaque through the synthesis of slimy, extracellular and cell-surface polysaccharides.

The extracellular streptococcal glucans are composed of glucosyl units linked in $\alpha$ 1,3 and $\alpha$ 1,6 configurations. Past attempts to control dental plaque formation with plaque-dispersing glucanohydrolases such as dextranase which hydrolyze 1,6-glucosyl linkages have had only limited success because the dextranase enzymes only partially degrade the glucans while leaving a water-insoluble residue. Recent investigations, in fact, have shown that this residual material is composed primarily of 1,3-linked glycosyl units with relatively few 1,6 linkages. While sources of 1,3 glucanohydrolases have been reported, the same are presently not commercially available. In addition, while an enzyme called mutanase has been isolated and was believed to be a 1,3-glucanohydrolase, the same, in spite of recent success as an anticaries agent in animal experiments, has only proved to be partially effective even in combination with dextranase as a means of degrading the streptococcal polysaccharides.

Thus, while dextranase has been proposed to be an effective caries preventive agent useful in the removal of bacteria on dextran containing plaque, the same has not been as successful as envisioned. Enzymes such as commercially available Penicillium dextranase have insufficient time to degrade plaque polysaccharides to any significant extent when such enzymes are introduced to tooth surfaces by conventional mouthwash, toothpaste, etc., where normal salivary flow, gingival fluid, and dietary liquids tend to wash the tooth surfaces and remove or dilute water soluble components in contact with the tooth surface. Such clearance can be observed in a matter of minutes and is increased when salivary flow is stimulated by taste and chewing. In this regard, the pH of oral fluid has been found to vary from about 5.4 to 7.8 and to be mostly in the range of 6.2 to 7.4. Such oral fluids are found on the tooth enamel which is composed primarily of a form of calcium phosphate called hydroxyapatite. While dextranases will usually bind to hydroxyapatite at lower acidic pH, the retention of these enzymes may be diminished in the mouth by the coating of the teeth with proteins, mucins, or other organic films from saliva, dental plaque, etc., and by the tendency for the pH of the oral fluid to rise to the 6.2 to 7.4 range. Consequently, such enzymes have their best chance to contact the hydroxyapatite directly after the teeth have been cleaned.

Accordingly, the present invention has been developed to overcome the shortcomings of the above known and similar techniques and to provide modified plaque-dispersing enzymes for prolonged activity through improved adherence to enamel surfaces.

SUMMARY OF THE INVENTION

It is therefore an object of the invention to provide a dental substance having increased longevity when used as an oral composition.

Another object of the invention is to provide a plaque-dispersing enzyme that will exhibit an increased affinity to tooth surfaces.

A further object of the invention is to provide a modification of a glucanohydrolase molecule to increase the effectiveness in combating dental plaque.

Still another object of the invention is to provide a technique for modifying plaque-dispersing enzyme molecules with carrier molecules in the presence of a complexing reagent to increase the affinity of these enzymes to tooth surfaces.

In order to accomplish the above and other objects, a plaque-dispersing glucanohydrolase such as dextranase is combined with a carrier such as a phosphoprotein or phosphoserine in the presence of a reacting agent such as ethyl chloroformate. The composition of such elements produces a modification of the glucanohydrolase enzyme by covalent cross linking of the enzyme with the carrier molecules causing the enzyme to have an increased affinity for the surfaces of the teeth. The molecular modification can be made with phosphate carrier groups having an organic or inorganic phosphate donor such that the same are covalently linked with the enzyme molecule upon the introduction of the complexing reagent. The increased binding capacity for hydroxyapatite components of the teeth, without loss of catalytic activity, results in a highly desirable extension of time during which an enzyme can combat plaque materials.

Other objects, advantages, and novel features of the invention will become apparent from the following detailed description of the invention:

DETAILED DESCRIPTION OF A PREFERRED EMBODIMENT

As has been previously noted, the build-up of plaque on teeth is caused by the generation of certain adhesive products by cariogenic organisms present in the fluids of the mouth. Such organisms as have been identified as *Streptococcus mutans* and Actinomyces produce polysaccharides forming the plaque deposits. In combating these deposits, plaque-dispersing agents are normally delivered to the mouth in the form of a mouthwash, toothpaste, etc., with the intent to actively degrade and reduce the build-up. As used in this disclosure, the term plaque-dispersing agent or enzyme is meant to encompass any substance which actively degrades the adhesive metabolic products of oral organisms which cause the identified plaque formation. In particular, such plaque-dispersing agents include those substances capable of actively degrading glucan deposits formed by the streptococcal organisms and polysaccharide deposits formed by the Actinomyces strains and any other adhesive deposits contributing to the formation of plaque as may be produced by any other variety of microbial organism. Accordingly, plaque-dispersing enzymes of the type contemplated by this disclosure include such substances as dextranase, glucanohydrolases which may be used to degrade $\alpha$ 1,3 and $\alpha$ 1,6 glucosidic linkages and polysaccharidases necessary to degrade polysaccharides. Still other plaque-dispersing enzymes such as proteases may be considered for use either singularly or in combination with dextranase depending on the type of deposit to be degraded. All of the identified enzymes may be obtained from conventional sources as may be known in the art or as may be subsequently produced. In particular, the dextranases may be obtained using the procedure of Simonson et al., as described in the article "Characterization of an Extracellular Dextranase from *Fusarium moniliforme*" in *Applied Microbiology*, Vol. 30, pp 855–861, 1975 or of Bowen as described in the article "Effects of Dextranase on Cariogenic and Non-Cariogenic Dextrans" in the *British Dental Journal*, Vol. 124, pp 347–349, 1968. The glucanohydrolase may likewise be formed as described by Reese et al., in the article "1,3-Glucanases of Fungi and Their Relationship to Mycodextranase" in the *Proceedings of the IVth International Fermentation Society: Fermentation Technology Today*, pp 735–742, 1972, or as described by Hasegawa et al., in the article "Enzymes that Hydrolyze Fungal Cell Wall Polysaccharides" in the *Journal of Biological Chemistry*, Vol. 244, pp 5460–5470, 1969.

While plaque-dispersing enzymes have been shown to be partially effective in degrading plaque deposits that form on the teeth, the same have suffered from deficiencies when employed in the mouth environment. In particular, the inability of the particular plaque-dispersing agent to effectively combat plaque has been attributed to its inability to remain in contact with the hydroxyapatite of the tooth surface for a time sufficient to enable substantial activity, especially in the presence of oral fluids having a pH greater than 6.0. Such enzymes can be effective if applied to clean tooth surfaces without the presence of other substances which tend to dilute and wash away the applied enzyme. However, the normal dispersion caused by salivary flow and mixture with ingested liquids has been sufficient to prevent enzyme retention for any significant length of time.

According to the present invention, therefore, a known plaque-dispersing enzyme is molecularly modified to enable the same to be retained by the tooth surfaces in a pH in excess of 6.0 for prolonged periods of time in spite of the previously mentioned problems. More specifically, the plaque-dispersing enzyme is bonded to a carrier agent having a strong affinity to the substances composing the tooth surface to enable the enzyme to be retained for much longer periods. As used in this context, the term carrier is defined to be any substance that has an affinity for the tooth surface and materials deposited thereon that is greater than the affinity of the enzyme, and which is capable of being used as an orally ingested substance. More particularly, a biological carrier is used and is defined as any biologically produced molecule or modification thereof that has an affinity for tooth surfaces greater than the enzyme, wherein "biologically produced" means any material produced by or acquired from a living organism. By way of example, the carrier agent may include such substances as phosphoproteins (phosvitin) and phosphoserine although these are only meant to be exemplary of those elements that may form the carrier agent. In accordance with the data provided by experiments using the present technique, phosphoproteins in particular have been found to have a very high affinity for the hydroxyapatite substances which form the primary composition of the teeth.

In order to provide the bonding between carrier and plaque-dispersing enzyme to provide the characteristic of increased affinity to tooth surfaces, a complexing reagent must be employed. The term complexing reagent is defined as any agent capable of effecting the linking of the carrier to the enzyme (typically by the formation of a covalent bond). More specifically, reagents which can be considered to bring about such bonding are exampled by such materials as glutaraldehyde, ethyl chloroformate and hexamethylene diisocyanate (HDC), although the same are not limited thereto and are only meant to be exemplary of those that may cause the formation of a molecular bond between the carrier and plaque-dispersing enzyme. Accordingly, it is readily recognized that different complexing reagents will be required depending on the materials used for the particular enzyme and the carrier which will in turn depend on the particular plaque deposit to be degraded.

In accordance with the present technique, the new substance for combating plaque build-up is produced by mixing the complexing agent with the carrier molecule prior to incorporation of the plaque-dispersing enzyme. The individual elements may be combined by any conventional mixing technique and the modified enzymes are then subsequently delivered in a vehicle suitable as an oral mouthwash, toothpaste, etc. The modifications created in the molecular structure of the enzyme cause the same to become immobilized for increased periods of time to thereby enable continuous catalytic activity on the surface of the teeth. In particular, the enzyme focuses on the hydrolysis of the microbial glucans or other microbial materials involved in the adherence and aggregation of cariogenic bacteria found in plaque. By modification, the problems produced by the dilution of salivation, etc., are significantly reduced.

While various plaque-dispersing enzymes, carriers, and complexing reagents have been referred to, the particular quantities and combinations will be dependent upon the type of plaque to be degraded. By way of example, however, certain of the identified substances were combined to illustrate the effect of the molecular modification on the activity of the plaque-dispersing enzymes. More specifically, dextranase from either Penicillium or *Fusarium moniliforme* was utilized as an enzyme from solutions of purified or improved extracts. The enzymes were employed in the range of 1.0–5.0 ml of solutions having protein concentrations from 0.05 to 1.3 mg/ml. The phosphoprotein phosvitin and phosphoserine were employed as the carriers and were prepared in buffers for use in the reaction in quantities of from 0.5 to 100 mg. In this regard, generally 1–2 ml of a 1 or 5 mg/ml solution was used. The complexing reagent employed with the particularly identified enzymes and carriers included glutaraldehyde, aqueous 25% (w/v); ethyl chloroformate, undiluted; and hexamethylene diisocyanate (HDC) 3.68 mg/ml of acetone. Generally, the complexing reactions were performed at 4° C. over a pH range of from 5.5–7.5. Reaction buffers were additionally employed using a 0.2M sodium acetate, pH 5.5 and 0.1M Tris chloride, pH 7.5. All observations were made to determine the percent retention of relative original activity of the active enzyme following molecular modification. In addition, the effects of using a protective dextran substrate were compared with retention without such use. In those cases, a 6% (w/v) dextran solution was used and the final dextran concentration in the reaction mixture was about 1.5%. The effects of the combination of carrier and plaque-dispersing enzyme produced using the above materials are more particularly shown in the following examples wherein specific reference will be made to the indicated tables. In regard to these tables, it should be recognized that the percentages are subject to normal scientific measurement error which accounts for certain percentages of relative original activity exceeding 100%.

In the example of Table I, ethyl chloroformate was used as the complexing reagent with phosvitin or phosphoserine acting as the carrier for the dextranase enzyme. The additives were reacted at neutral pH of 6.8–7.2 and stored at 4° C. In the present example, it can be seen that phosphoserine was not a very suitable carrier under the particular conditions employed. However, when phosvitin was used, between 13% and 35% of the original dextranase activity was retained following the reaction as compared with only a 9% figure when no carrier was present.

TABLE I

An Example
Of The Retention Of Relative Activity Of Dextranases
Following Reaction With Ethyl Chloroformate (EtC)
As The Complexing Reagent Is As Follows:

| Source of Dextranase | EtC (ml)* | Carrier** | %RA*** |
|---|---|---|---|
| *Fusarium* | 0 | phosvitin | 100 |
| " | 0.10 | " | 13 |
| "0 | phosphoserine | 100 | |
| " | 0.10 | " | 0 |
| "0.10 | none | | 9 |
| *Penicillium* | 0.06 | phosvitin | 100 |
| " | 0.06 | " | 35 |

*Ethyl chloroformate was added as 0.8 ml/g of protein reactants
**The ratio (w/w) of reactants was 1:9 (dextranase:carrier)
***The % retention of relative original activity In Table II, glutaraldehyde was used as the complexing reagent to molecularly bond the dextranase and phosvitin carrier. As can be seen, the % retention of relative original activity was found to be greater for this complexing reagent than for ethyl chloroformate. It was also found that the percent retention decreased as the amount of complexing reagent gluteraldehyde was increased. In addition, the comparison between the presence of a dextran substrate and the absence of the same substrate was made in this example. The effect of the addition of the dextran is shown to significantly improve the percent retention of relative original activity in comparison to when dextran was absent. This effect is apparently due to the protection of amino acid residues of the enzyme which are at or near the active sites during catalytic activity.

TABLE II

An Example
Of The Retention Of Relative Activity Of The Dextranase
Following Reaction With Glutaraldehyde As The Complexing
Reagent Is As Follows:

| glutaraldehyde reagent (ml) | final concen. of glutar. (%) | Dextran Absent | | Dextran Present | |
|---|---|---|---|---|---|
| | | Activity (Units /ml) | %RA* | Activity (Units /ml) | %RA* |
| 0 | 0 | 510 | 100 | 500 | 100 |
| 0.05 | 1.67 | 320 | 63 | 480 | 96 |
| 0.10 | 3.33 | 190 | 37 | 400 | 80 |
| 0.20 | 6.67 | 120 | 24 | 240 | 48 |
| 0.30 | 10.00 | 70 | 14 | 220 | 44 |
| 0.50 | 16.67 | 70 | 14 | 80 | 16 |
| 1.00 | 33.33 | 80 | 16 | 80 | 16 |

*The % retention of relative original activity

In Table III hexamethylene diisocyanate (HDC) was used as the complexing reagent to combine the dextranase enzyme with the phosvitin carrier. Again, a high proportion of the original activity was retained using this particular complexing reagent and the effect of a dextran substrate was to likewise increase the percent retention of relative original activity. From a comparison of Table III with the previous Table I and II it is readily apparent that the selection of the complexing reagent is important in obtaining optimal percent retention of relative original activity for a particular enzyme and carrier molecule. In this example, HDC was significantly more beneficial as a complexing reagent when phosvitin was used with dextranase.

TABLE III

An Example Of The Retention Of Relative Activity Of The Dextranase
Following Reaction With Hexamethylene Diisocyanate (HDC)
As The Complexing Reagent Is As Follows:

| HDC reagent (ml) | Final Concen. of HDC (mg%,w/v) | Dextran Absent | | Dextran Present | |
|---|---|---|---|---|---|
| | | Activity (Units/ml) | %RA* | Activity (Units/ml) | %RA* |
| 0 | 0 | 380 | 100 | 420 | 100 |
| 0.25 | 23 | 320 | 84 | 480 | 114 |
| 0.50 | 46 | 260 | 68 | 380 | 91 |
| 0.75 | 69 | 220 | 58 | 420 | 100 |
| 1.00 | 92 | 200 | 52 | 400 | 95 |

*The retention of relative original activity

While the intent of the present technique is to prolong the activity of the plaque-dispersing enzyme to enable it to act for longer periods of time on the tooth surface, the stability of the complexing mixture was also investigated. In this regard, Table IV shows that the HDC-dextranphosvitin complex was stable over a seven-day period. Thus, in addition to having the benefits of prolonged activity, the mixture did not appear to exhibit any loss of activity for a substantial period of storage.

TABLE IV

An Example Of Stability Of HDC Reacted Dextranase, In The Presence Of
Dextran Over A 7-Day Period. Phosvitin Was Used As The Carrier*

| HDC reagent (ml) | Final Concen. of HDC (mg%,w/v) | Per Cent Retention of Relative Original Activity | | | | |
|---|---|---|---|---|---|---|
| | | day 1 | day 2 | day 3 | day 6 | day 7 |
| 0 | 0 | 100 | 100 | 100 | 100 | 100 |

TABLE IV-continued
An Example Of Stability Of HDC Reacted Dextranase, In The Presence Of Dextran Over A 7-Day Period. Phosvitin Was Used As The Carrier*

| HDC reagent (ml) | Final Concen. of HDC (mg%,w/v) | Per Cent Retention of Relative Original Activity | | | | |
|---|---|---|---|---|---|---|
| | | day 1 | day 2 | day 3 | day 6 | day 7 |
| 0.25 | 23 | 96 | 95 | 100 | 118 | 103 |
| 0.50 | 46 | 91 | 93 | 94 | 97 | 95 |
| 0.75 | 69 | 87 | 88 | 117 | 97 | 103 |
| 1.00 | 92 | 91 | 85 | 103 | 97 | 97 |

*Phosvitin was present at a final concentration of 25%,w/v. The reaction mixtures were stored at 4° C. Dextran was present at a final concentration of 1.5%.

As can be seen from the above description, the modification of a plaque-dispersing enzyme with an appropriate carrier may increase the affinity of the enzyme to the substances of the tooth surface. The prolonged activity provided by such modification enables the dissolution and dispersion of the plaque material that would otherwise not be effected by normal oral delivery of a plaque-dispersing enzyme. The particular enzymes may be chosen based on their effectiveness against a specific plaque deposit or they may be combined to produce a composition which will combat a plaque deposit in the most optimal manner. The particular quantities, concentrations, and combinations will depend on the individual substances to be combined. The invention, therefore, contemplates the use and modification of individual plaque-dispersing enzymes as well as any combinations of enzymes which will act to prevent dental caries and periodontal diseases. Likewise, the particular desirability of employing a dextran substrate with the modified carrier will depend upon the specific combination of substances chosen.

While the invention has been described with reference to particular enzymes, carriers and complexing reagents, it should be noted that the same should be chosen to achieve the optimal activity for any combination. Thus, as was shown by the tables, the type and quantity of carrier should be selected to provide a modified enzyme with optimal retention of relative original activity. Likewise, the type and quantity of complexing reagent should be selected to retain the optimal percentage of original activity of the enzyme when used with a particular enzyme and carrier.

Obviously, many other variations and modifications of the present invention are possible in light of the above teachings. It is therefore to be understood that within the scope of the appended claims the invention may be practiced otherwise than as specifically described.

What is claimed and desired to be secured by letters patent of the United States is:

1. A technique for degrading plaque on the surfaces of teeth in the mouth cavity comprising:
   forming a modified plaque-dispersing enzyme by,
      selecting a plaque-dispersing enzyme,
      selecting a carrier agent having an affinity for tooth surfaces greater than said plaque-dispersing enzyme, and
      bonding said plaque-dispersing enzyme and carrier by reacting the same with a complexing reagent to form a modified enzyme having an affinity for tooth surfaces greater than the selected enzyme; and
   introducing said modified enzyme into the mouth cavity to contact said teeth.

2. The technique of claim 1 wherein the step of introducing comprises introducing the modified enzyme into a mouth cavity having a pH in excess of 6.0.

3. The technique of claim 2 wherein said pH is in the range of 6.8-7.2.

4. The technique of claim 1 wherein the step of selecting the carrier comprises selecting a biological carrier as said carrier agent.

5. The technique of claim 4 wherein said biological carrier is selected from the group consisting of phosphoserine and phosphoproteins.

6. The technique of claim 4 wherein said biological carrier is a phosphoprotein.

7. The technique of claim 6 wherein said phosphoprotein is phosvitin.

8. The technique of claim 4 wherein said biological carrier is phosphoserine.

9. The technique of claim 4 wherein said complexing reagent is selected from the group consisting of glutaraldehyde, ethyl chloroformate, and hexamethylene diisocyanate (HDC).

10. The technique of claim 4 wherein said plaque-dispersing enzyme is selected from the group consisting of glucanohydrolases and polysaccharidases.

11. The technique of claim 4 wherein said plaque-dispersing enzyme is dextranase.

12. The technique of claim 4 wherein said plaque-dispersing enzyme is protease.

13. The technique of claim 4 wherein said step of introducing comprises introducing the modified enzyme into a mouth cavity having a pH in excess of 6.0.

14. The technique of claim 1 wherein said bonding step includes bonding said carrier and enzyme in the presence of a substrate of the enzyme to increase the retention of enzyme activity.

15. A technique for degrading plaque on the surfaces of teeth in the mouth cavity comprising:
   forming a modified plaque-dispersing enzyme by,
      selecting a plaque-dispersing enzyme from the group consisting of glucanohydrolases and polysaccharidases,
      selecting a biological carrier agent having an affinity for tooth surfaces greater than said plaque-dispersing enzyme from the group consisting of phosphoserine and phosphoproteins; and
      bonding said plaque-dispersing enzyme and carrier by reacting the same with a complexing reagent to form a modified enzyme having an affinity for tooth surfaces greater than the selected enzyme; and
   introducing said modified enzyme into the mouth cavity to contact said teeth.

16. The technique of claim 15 wherein said carrier is phosphoserine.

17. The technique of claim 15 wherein said carrier is a phosphoprotein.

18. The technique of claim 17 wherein said phosphoprotein is phosvitin.

19. The technique of claim 15 wherein said complexing reagent is selected from the group consisting of glutaraldehyde, ethyl chloroformate, and hexamethylene diisocyanate (HDC).

20. The technique of claim 15 wherein said plaque-dispersing enzyme is dextranase.

21. The technique of claim 15 wherein said plaque-dispersing enzyme is protease.

22. The technique of claim 15 wherein said step of introducing comprises introducing the modified enzyme into a mouth cavity having a pH in excess of 6.0.

23. The technique of claim 15 wherein said bonding step includes bonding said carrier and enzyme in the presence of a substrate of the enzyme to increase the retention of enzyme activity.

* * * * *